United States Patent
Lang et al.

(10) Patent No.: US 10,433,715 B2
(45) Date of Patent: *Oct. 8, 2019

(54) ENDOSCOPE CONTROL UNIT WITH BRAKING SYSTEM

(71) Applicant: Endochoice, Inc., Alpharetta, GA (US)

(72) Inventors: Alexander Lang, Wedel (DE); Stephan Wieth, Klein Nordende (DE)

(73) Assignee: EndoChoice, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/921,051

(22) Filed: Mar. 14, 2018

(65) Prior Publication Data
US 2018/0199796 A1   Jul. 19, 2018

Related U.S. Application Data

(63) Continuation of application No. 14/835,996, filed on Aug. 26, 2015, now Pat. No. 9,949,623, which is a
(Continued)

(51) Int. Cl.
*A61B 1/005* (2006.01)
*A61B 1/008* (2006.01)
(Continued)

(52) U.S. Cl.
CPC ........ *A61B 1/0052* (2013.01); *A61B 1/00006* (2013.01); *A61B 1/008* (2013.01);
(Continued)

(58) Field of Classification Search
CPC .......... A61M 25/0133; A61M 25/0136; A61M 25/0138; A61M 25/0141; A61M 25/0144;
(Continued)

(56) References Cited

U.S. PATENT DOCUMENTS

| 4,027,697 A | 6/1977 | Bonney |
| 4,084,401 A | 4/1978 | Belardi |

(Continued)

FOREIGN PATENT DOCUMENTS

| CA | 2297986 | 3/1999 |
| CA | 2765559 | 12/2010 |

(Continued)

OTHER PUBLICATIONS

Internatonal Search Report for PCT/US14/38094, dated Nov. 6, 2014.
International Search Report for PCT/US14/37004, dated Sep. 25, 2014.
International Search Report for PCT/US2014/037526, dated Oct. 16, 2014.
International Search Report for PCT/US2015/012751, dated Jun. 26, 2015.
International Search Report for PCT/US2014/58143, dated Jan. 21, 2015.

(Continued)

*Primary Examiner* — Ryan N Henderson
(74) *Attorney, Agent, or Firm* — Bookoff McAndrews, PLLC

(57) ABSTRACT

A control unit that includes a braking system for fixing the position of an endoscope tip is provided. The control system includes an up-down control knob and a right-left control knob. The brakes are engaged by rotating the control knob itself counter-clockwise from a free wheeling position. After the brakes have been engaged, a sufficient amount of force applied to the control knobs will move the endoscope tip slightly in the corresponding direction, allowing for fine tuning of tip position after braking.

18 Claims, 11 Drawing Sheets

Related U.S. Application Data continuation-in-part of application No. 14/278,221, filed on May 15, 2014, now abandoned.

(60) Provisional application No. 61/837,108, filed on Jun. 19, 2013, provisional application No. 61/824,634, filed on May 17, 2013.

(51) Int. Cl.
*A61M 25/01* (2006.01)
*A61B 1/00* (2006.01)
*G02B 23/24* (2006.01)
*A61B 17/00* (2006.01)

(52) U.S. Cl.
CPC .......... *A61B 1/0051* (2013.01); *A61B 1/0057* (2013.01); *A61B 1/00147* (2013.01); *A61M 25/0133* (2013.01); *A61M 25/0136* (2013.01); *A61M 25/0147* (2013.01); *G02B 23/2476* (2013.01); *A61B 2017/00318* (2013.01); *A61B 2017/00323* (2013.01); *A61B 2017/00327* (2013.01)

(58) Field of Classification Search
CPC .......... A61M 25/0147; A61M 25/0152; A61M 25/0155; A61M 25/0158; A61M 25/0161; A61M 25/0163; A61B 2017/003; A61B 2017/00305; A61B 2017/00309; A61B 2017/00314; A61B 2017/00318; A61B 2017/00323; A61B 2017/00327; A61B 2017/00331; A61B 2017/2908; A61B 2017/00292; A61B 2017/00296; A61B 1/005; A61B 1/0051; A61B 1/0052; A61B 1/0053; A61B 1/0055; A61B 1/0056; A61B 1/0057; A61B 1/0058; A61B 1/008; A61B 1/01
See application file for complete search history.

(56) References Cited

U.S. PATENT DOCUMENTS

| | | |
|---|---|---|
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,489,256 A | 2/1996 | Adair |
| 5,518,501 A | 5/1996 | Oneda |
| 5,518,502 A | 5/1996 | Kaplan |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,662,588 A | 9/1997 | Iida |
| 5,674,182 A | 10/1997 | Suzuki |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,810,715 A | 9/1998 | Moriyama |
| 5,836,894 A | 11/1998 | Sarvazyan |
| 5,860,913 A | 1/1999 | Yamaya |
| 5,870,234 A | 2/1999 | EbbesmeiemeeSchitthof |
| 5,916,148 A | 6/1999 | Tsuyuki |
| 5,940,126 A | 8/1999 | Kimura |
| 6,095,970 A | 8/2000 | Hidaka |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 | 8/2001 | Yoon |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,638,214 B2 | 10/2003 | Akiba |
| 6,673,012 B2 | 1/2004 | Fujii |
| 6,712,760 B2 | 3/2004 | Sano |
| 6,832,984 B2 | 12/2004 | Stelzer |
| 6,888,119 B2 | 5/2005 | Iizuka |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,447,132 B1 | 5/2013 | Galil |
| 8,449,457 B2 | 5/2013 | Aizenfeld |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,314,147 B2 | 4/2016 | Levy |
| 9,320,419 B2 | 4/2016 | Kirma |
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109774 A1 | 8/2002 | Meron |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |

(56) References Cited

U.S. PATENT DOCUMENTS

| | | |
|---|---|---|
| 2003/0083552 A1 | 5/2003 | Remijan |
| 2003/0128893 A1 | 7/2003 | Castorina |
| 2003/0153897 A1 | 8/2003 | Russo |
| 2003/0187328 A1 | 10/2003 | Seki et al. |
| 2004/0015054 A1 | 1/2004 | Hino |
| 2004/0046865 A1 | 3/2004 | Ueno |
| 2004/0061780 A1 | 4/2004 | Huffman |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0090709 A1 | 4/2005 | Okada |
| 2005/0096501 A1 | 5/2005 | Stelzer |
| 2005/0119527 A1 | 6/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0283048 A1 | 12/2005 | Gill |
| 2005/0283049 A1 | 12/2005 | Seki et al. |
| 2006/0047184 A1 | 3/2006 | Banik |
| 2006/0063976 A1 | 3/2006 | Aizenfeld |
| 2006/0069314 A1 | 3/2006 | Farr |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0106119 A1 | 5/2007 | Hirata |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | DeLorme |
| 2007/0213591 A1 | 9/2007 | Aizenfeld |
| 2007/0229656 A1 | 10/2007 | Khait |
| 2007/0244353 A1 | 10/2007 | Larsen |
| 2007/0244354 A1 | 10/2007 | Bayer |
| 2007/0247867 A1 | 10/2007 | Hunter |
| 2007/0265492 A1 | 11/2007 | Sonnenschein |
| 2007/0270642 A1 | 11/2007 | Bayer |
| 2007/0279486 A1 | 12/2007 | Bayer |
| 2007/0293720 A1 | 12/2007 | Bayer |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 9/2008 | Seibel et al. |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2011/0034769 A1 | 2/2011 | Adair |
| 2011/0063427 A1 | 3/2011 | Fengler |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1* | 11/2012 | Hoshino ............ A61B 1/00066 600/146 |
| 2012/0300999 A1 | 11/2012 | Bayer |
| 2013/0053646 A1 | 2/2013 | Yamamoto |
| 2013/0057724 A1 | 3/2013 | Miyahara |
| 2013/0066297 A1 | 3/2013 | Shtul |
| 2013/0085329 A1 | 4/2013 | Morrissette |

(56) References Cited

U.S. PATENT DOCUMENTS

| | | |
|---|---|---|
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0150671 A1 | 6/2013 | Levy |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | | | |
|---|---|---|---|---|
| CA | 2812097 | 3/2012 | | |
| CA | 2798716 | 6/2013 | | |
| CA | 2798729 | 6/2013 | | |
| CN | 103348470 | 10/2013 | | |
| CN | 103403605 | 11/2013 | | |
| CN | 103491854 | 1/2014 | | |
| CN | 103702604 | 4/2014 | | |
| CN | 103732120 | 4/2014 | | |
| CN | 104717916 | 6/2015 | | |
| CN | 105246393 | 1/2016 | | |
| CN | 105324065 | 2/2016 | | |
| CN | 105324066 | 2/2016 | | |
| CN | 105338875 | 2/2016 | | |
| CN | 105358042 | 2/2016 | | |
| CN | 105358043 | 2/2016 | | |
| CN | 105377106 | 3/2016 | | |
| CN | 105407788 | 3/2016 | | |
| DE | 202010016900 | 5/2011 | | |
| EP | 1690497 | 8/2006 | | |
| EP | 1835844 | 9/2007 | | |
| EP | 1968425 | 9/2008 | | |
| EP | 1986541 | 11/2008 | | |
| EP | 1988813 | 11/2008 | | |
| EP | 2023794 | 2/2009 | | |
| EP | 2023795 | 2/2009 | | |
| EP | 2190341 | 6/2010 | | |
| EP | 2211683 | 8/2010 | | |
| EP | 2457492 | 5/2012 | | |
| EP | 2457493 | 5/2012 | | |
| EP | 1988812 | 11/2012 | | |
| EP | 2520218 | 11/2012 | | |
| EP | 2604175 | 6/2013 | | |
| EP | 2618718 | 7/2013 | | |
| EP | 2635932 | 9/2013 | | |
| EP | 2648602 | 10/2013 | | |
| EP | 2649648 | 10/2013 | | |
| EP | 2672878 | 12/2013 | | |
| EP | 2736400 | 6/2014 | | |
| EP | 2744390 | 6/2014 | | |
| EP | 2442706 | 11/2014 | | |
| EP | 2865322 | 4/2015 | | |
| EP | 2908714 | 8/2015 | | |
| EP | 2979123 | 2/2016 | | |
| EP | 2991537 | 3/2016 | | |
| EP | 2994032 | 3/2016 | | |
| EP | 2994033 | 3/2016 | | |
| EP | 2994034 | 3/2016 | | |
| EP | 2996536 | 3/2016 | | |
| EP | 2996541 | 3/2016 | | |
| EP | 2996542 | 3/2016 | | |
| EP | 2996621 | 3/2016 | | |
| GB | 12196628 | 3/2015 | | |
| JP | H1043129 | 2/1998 | | |
| JP | H10239740 | 9/1998 | | |
| JP | 11137512 | 5/1999 | | |
| JP | 2004313806 A | * 11/2004 | ........... | A61B 1/0052 |
| JP | 2005253543 | 9/2005 | | |
| JP | 2006025888 | 2/2006 | | |
| JP | 2006068109 | 3/2006 | | |
| JP | 2010178766 A | 8/2010 | | |
| JP | 2012135432 | 7/2012 | | |
| JP | 2013116277 A2 | 6/2013 | | |
| JP | 2013123647 | 6/2013 | | |
| JP | 2013123648 | 6/2013 | | |
| JP | 2013208459 | 10/2013 | | |
| JP | 2013215582 | 10/2013 | | |
| JP | 2013230383 | 11/2013 | | |
| JP | 2013542467 | 11/2013 | | |
| JP | 2013544617 | 12/2013 | | |
| JP | 2014524303 | 9/2014 | | |
| JP | 2014524819 | 9/2014 | | |
| JP | 2015533300 | 11/2015 | | |
| WO | 2006073676 | 7/2006 | | |
| WO | 2006073725 | 7/2006 | | |
| WO | 2007070644 | 6/2007 | | |
| WO | 2007092533 | 8/2007 | | |
| WO | 2007092636 | 8/2007 | | |
| WO | 2007087421 | 11/2007 | | |
| WO | 2007136859 | 11/2007 | | |
| WO | 2007136879 | 11/2007 | | |
| WO | 2008015164 | 2/2008 | | |
| WO | 2009014895 | 1/2009 | | |

(56) References Cited

FOREIGN PATENT DOCUMENTS

| | | |
|---|---|---|
| WO | 2009015396 | 1/2009 |
| WO | 2009049322 | 4/2009 |
| WO | 2009049324 | 4/2009 |
| WO | 2009062179 | 5/2009 |
| WO | 20100146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

International Search Report for PCT/US2014/071085, dated Mar. 27, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66486, dated Dec. 17, 2015.
International Search Report for PCT/US2015/6548, dated Feb. 26, 2016.
Office Action dated Feb. 26, 2016 for U.S. Appl. No. 14/274,323.
Office Action dated Feb. 4, 2016 for U.S. Appl. No. 14/271,234.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.

\* cited by examiner

ENDOSCOPE CONTROL UNIT WITH BRAKING SYSTEM

CROSS-REFERENCE

This application is a continuation of U.S. patent application Ser. No. 14/835,996, filed on Aug. 26, 2015, now U.S. Pat. No. 9,949,623, issued Apr. 24, 2018, which is a continuation-in-part application of U.S. patent application Ser. No. 14/278,221, filed on May 15, 2014, now abandoned, which claims the benefit of priority of U.S. Provisional Application No. 61/824,634, filed on May 17, 2013, and U.S. Provisional Application No. 61/837,108, filed on Jun. 19, 2013, all of which are incorporated by reference herein in their entireties.

FIELD

The present specification relates generally to endoscopes, and more specifically, to a control unit comprising a braking system for maneuvering the tip of an endoscope and fixing the tip at a desired position.

BACKGROUND

An endoscope is a medical instrument used for examining and treating internal body parts such as the alimentary canals, airways, the gastrointestinal system, and other organ systems. Conventionally used endoscopes have at least a flexible tube carrying a fiber optic light guide for directing light from an external light source situated at a proximal end of the tube to a distal tip. Also, most endoscopes are provided with one or more channels, through which medical devices, such as forceps, probes, and other tools, are passed. Further, during an endoscopic procedure, fluids, such as water, saline, drugs, contrast material, dyes, or emulsifiers are often introduced or evacuated via the flexible tube. A plurality of channels, one each for introduction and suctioning of liquids, may be provided within the flexible tube.

Endoscopes have attained great acceptance within the medical community since they provide a means for performing procedures with minimal patient trauma while enabling the physician to view the internal anatomy of the patient. Over the years, numerous endoscopes have been developed and categorized according to specific applications, such as cystoscopy, colonoscopy, laparoscopy, and upper GI endoscopy among others. Endoscopes are usually inserted into the body's natural orifices or through an incision in the skin.

In many endoscopes the distal end of an insertion tube is capable of being articulated by a steering mechanism that includes a pair of external control wheels coupled to steering cables mounted inside the insertion tube. Rotation of one of the control wheels produces an up or down deflection of the distal tip of the insertion tube while rotation of the second control wheel produces a left or right deflection of the insertion tube tip. By operating the two control wheels, the distal end of the insertion tube can be pointed at a desired target within the range of the instrument or maneuvered through a tortuous path of travel.

Further, the control wheels or knobs are locked through respective braking mechanisms, thereby causing the distal end of the insertion tube to be fixed in a desired position.

For example, German patent application DE 20 2011 109 769 U1, filed on Jul. 1, 2011 and assigned to the applicant of the present specification, discloses an endoscope having an articulation unit. The deflection of the articulation unit (also called curvature device), and thus of the distal end of the endoscope is effected by means of cables. In each case, two cables arranged opposite each other on the outer circumference of the articulation unit are connected to form a cable pair. The cable pairs are attached in such a way to cable drums that can be adjusted by rotary knobs so that the distal end of the articulation unit carries out a movement upwards or downwards (up/down; U-D) or a movement in a direction right or left (right/left; R-L).

When a human body is examined using an endoscope having an articulation unit, on occasions it can be advantageous to fix the deflection of the articulation unit. As mentioned, usually this is accomplished by means of a locking device, also called a brake, that prevents the cable drum(s) from rotating.

Known braking or locking devices often are of a complicated design. What is needed is an efficient braking system that enables an operating physician to easily fix the endoscope insertion tube tip in a desired position when required and just as easily move the tip in a desired direction.

There is therefore a need for a system that ensures smooth directional readjustment of right and left (or up and down) movement of the insertion tube tip after applying a brake for fixing the end position. There is also need for a watertight braking system that provides a complete separation of free movement and locking operations.

SUMMARY

A control unit for use with an endoscope for maneuvering the tip of a distal end of an endoscope insertion tube is provided. The endoscope tip is easily moved in up and down as well as right and left directions by using the control unit of the present specification.

The control unit includes a braking system that allows for fixing the position of the endoscope tip.

The present specification discloses a control unit providing a braking system for an articulation unit of endoscope, said control unit comprising: a first shaft having a first end and a second end, the first end being coupled with a first operating knob, the second end being coupled with a first cable drum and a first cable pair that are coupled with the articulation unit of the endoscope, wherein at least a portion of the first shaft in proximity to the first operating knob includes a space; a second hollow shaft having a first end and a second end, the first end being coupled with a second operating knob, the second end being coupled with a second cable drum and a second cable pair that are coupled with the articulation unit of the endoscope, wherein the first shaft is positioned within the second shaft; a brake knob rotatable about its center axis; a stationary sleeve arranged between the first and the second shafts; a spring supported by the first shaft in proximity to the first end of the first shaft; a pin extending into the space of the first shaft and coupled to said brake knob by the spring, wherein said pin has a first position and a second position; and at least one brake body extending outwardly from said pin, wherein said at least one brake body does not press against the stationary sleeve when the pin is in the first position; wherein the pin is movable from the first position into the second position by rotational motion of said brake knob in a first rotational direction and compression of said spring, wherein said at least one brake body becomes pressed against said stationary sleeve when said pin is in said second position, thereby locking said first shaft and braking the articulation unit in a predetermined direction, and wherein said pin is movable from said second position into said first position by rotational motion of said brake knob in a second rotational direction opposite said first rotational direction, thereby allowing the compressive force of said spring to push said pin into said first position.

Optionally, said pin includes at least two brake bodies.

The predetermined direction may be a right/left (R/L) direction.

The brake knob may be of concentric design and positioned above the first operating knob for braking the articulation unit in a predetermined direction.

Optionally, the pin is held in the second position by a latching mechanism. Still optionally, said latching mechanism comprises a control pin extending outwardly from said pin and a spiral groove having an upper portion and a lower portion with a recess formed in a wall of the first shaft. The control pin may be free to move within said spiral groove of said latching mechanism when said pin is in said first position. The control pin may be latched into said recess of said lower portion of said spiral groove when said pin is in said second position.

Optionally, a sealing element is provided between the first shaft and the first stationary sleeve.

The present specification also discloses a control unit providing a braking system for an articulation unit of endoscope, said control unit comprising: a first shaft having a first end and a second end, the first end being coupled with a first operating knob, the second end being coupled with a first cable drum, a first cable pair, and the articulation unit of the endoscope, at least a portion of the first shaft in proximity of the first operating knob including a space; a second hollow shaft having a first end and a second end, the first end being coupled with a second operating knob, the second end being coupled with a second cable drum, a second cable pair, and the articulation unit of the endoscope, the first shaft is positioned within the second shaft; a brake disc having a central opening through which said second shaft extends, said brake disc being in physical contact with the second shaft; a stationary sleeve surrounding at least a portion of the second shaft; a brake base positioned below said brake disc, having a central opening through which said second shaft extends and comprising a first control edge; a brake lid positioned above said brake base and said brake disc, coupled to said brake base, having a central opening through which said second shaft extends and comprising a second control edge; a spring positioned between said brake base and said brake lid; a brake bushing positioned between said brake base and said brake lid and below said brake disc, having a central opening through which said second shaft extends and being movable vertically between first and second brake bushing positions; and a brake handle attached to said brake base for rotating said brake base and brake lid; wherein said brake bushing is movable from said first position to said second position by rotating said brake handle in a first rotational direction, causing said brake bushing to move upward and compress said brake disc against said brake lid, thereby locking the second shaft and braking the articulation unit in a predetermined direction, further wherein said brake bushing is movable from said second position into said first position by rotational motion of said brake handle in a second rotational direction opposite said first rotational direction, allowing the compressive force of said spring to push said brake bushing into said first position.

The predetermined direction may be an up/down (U/D) direction.

The brake handle may be of concentric design and positioned below the second operating knob for braking the articulation unit in a predetermined direction.

Optionally, the brake base, lid, and bushing are supported by a housing surrounding the brake disc.

Optionally, the brake bushing comprises negative indentations on a surface for fitting into one or more positive indentations on a surface of the lid, compressing the brake bushing and the brake disc to the lid in the second position of the brake bushing. Optionally, in the first position of the brake bushing, the negative indentations on the surface of the brake bushing are not aligned with the positive indentations on the surface of the lid and the brake disc is freely movable.

The present specification also discloses an endoscope comprising a braking system for an articulation unit of the endoscope, said braking system comprising: a first shaft having a first end and a second end, the first end being coupled with a first operating knob, the second end being coupled with a first cable drum that is coupled with a first cable pair that is coupled with the articulation unit of the endoscope, at least a portion of the first shaft in proximity of the first operating knob having a space; a second hollow shaft having a first end and a second end, the first end being coupled with a second operating knob, the second end being coupled with a second cable drum that is coupled with a second cable pair that is coupled with the articulation unit of the endoscope, the first shaft is positioned within the second shaft; a right/left movement controller unit comprising: a brake knob rotatable about its center axis; a first stationary sleeve arranged between the first and the second shafts; a first spring being supported by the first shaft in proximity to the first end; a pin having a tapered distal end and extending into the space of the first shaft in a first pin position; and three brake bodies extending outwardly from said pin and positioned equidistant from one another about a periphery of said pin; wherein the pin is movable from the first pin position into a second pin position further into the space of the first shaft by rotational motion of said brake knob in a first brake knob rotational direction and compression of said first spring, wherein each of said brake bodies becomes pressed against said first stationary sleeve when said pin is in said second pin position, thereby locking said first shaft and braking the articulation unit in a first predetermined direction; further wherein said pin is movable from said second pin position into said first pin position by rotational motion of said brake knob in a second brake knob rotational direction opposite said first brake knob rotational direction, allowing the compressive force of said first spring to push said pin into said first pin position.

Optionally, said braking system further comprises an up/down movement controller unit comprising: a brake disc having a central opening through which said second shaft extends, said brake disc being in physical contact with the second shaft; a second stationary sleeve surrounding at least a portion of the second shaft; a brake base positioned below said brake disc, having a central opening through which said second shaft extends and comprising a first control edge; a brake lid positioned above said brake base and said brake disc, coupled to said brake base, having a central opening through which said second shaft extends and comprising a second control edge; a second spring positioned between said brake base and said brake lid; a brake bushing positioned between said brake base and said brake lid and below said brake disc, having a central opening through which said second shaft extends and being movable vertically between first and second brake bushing positions; and a brake handle attached to said brake base for rotating said brake base and brake lid; wherein said brake bushing is movable from said first brake bushing position to said second brake bushing position by rotating said brake handle in a first brake handle rotational direction, causing said brake bushing to move upward and compress said brake disc against said brake lid, thereby locking the second shaft and braking the articulation unit in a second predetermined direction, further wherein said brake bushing is movable from said second brake bushing position into said first brake bushing position by rotational motion of said brake handle in a second brake handle rotational direction opposite said first brake handle rotational direction, allowing the compressive force of said second spring to push said brake bushing into said first brake bushing position.

The pin may be held in the second pin position by a latching mechanism. Optionally, said latching mechanism comprises a control pin extending outwardly from said pin and a spiral groove having an upper portion and a lower portion with a recess formed in a wall of the first shaft. The control pin may be free to move within said spiral groove of said latching mechanism when said pin is in said first position and said control pin may be latched into said recess of said lower portion of said spiral groove when said pin is in said second position.

Optionally, a sealing element is provided between the first shaft and the first stationary sleeve.

Optionally, the brake bushing comprises negative indentations on a surface for fitting into one or more positive indentations on a surface of the lid, compressing the brake bushing and the brake disc to the lid in the second position of the brake bushing.

The present specification also discloses a control unit providing a braking system for an articulation unit of endoscope, said control unit comprising: a first shaft having a first end and a second end, the first end being coupled with a first operating knob, the second end being coupled with a first cable drum and a first cable pair that are coupled with the articulation unit of the endoscope, wherein at least a portion of the first shaft in proximity to the first operating knob is hollow; a second hollow shaft having a first end and a second end, the first end being coupled with a second operating knob, the second end being coupled with a second cable drum and a second cable pair that are coupled with the articulation unit of the endoscope, wherein the first shaft is positioned within the second shaft; a brake knob rotatable about its center axis; a stationary sleeve arranged between the first and the second shafts; a spring supported by the first shaft in proximity to the first end of the first shaft; a pin extending into the hollow portion of the first shaft and coupled to said brake knob by the spring, wherein said pin has a first position and a second position; and a brake body extending outwardly from said pin, wherein said brake body does not press against the stationary sleeve when the pin is in the first position; wherein the pin is movable from the first position into the second position by rotational motion of said brake knob in a first rotational direction and compression of said spring, wherein said brake body becomes pressed against said stationary sleeve when said pin is in said second position, thereby locking said first shaft and braking the articulation unit in a predetermined direction, and wherein said pin is movable from said second position into said first position by rotational motion of said brake knob in a second rotational direction opposite said first rotational direction, thereby allowing the compressive force of said spring to push said pin into said first position.

In one embodiment, the predetermined direction is a right/left (R/L) direction.

In one embodiment, the brake knob is of concentric design and positioned above the first operating knob for braking the articulation unit in a predetermined direction.

Optionally, in one embodiment, the pin is held in the second position by a latching mechanism. In one embodiment, the latching mechanism comprises a control pin extending outwardly from said pin and a spiral groove having an upper portion and a lower portion with a recess formed in a wall of the first shaft. In one embodiment, the control pin is free to move within said spiral groove of said latching mechanism when said pin is in said first position. In one embodiment, the control pin is latched into said recess of said lower portion of said spiral groove when said pin is in said second position.

Optionally, in one embodiment, a sealing element is provided between the first shaft and the first stationary sleeve.

The present specification also discloses a control unit providing a braking system for an articulation unit of endoscope, said control unit comprising: a first shaft having a first end and a second end, the first end being coupled with a first operating knob, the second end being coupled with a first cable drum, a first cable pair, and the articulation unit of the endoscope, at least a portion of the first shaft in proximity of the first operating knob being hollow; a second hollow shaft having a first end and a second end, the first end being coupled with a second operating knob, the second end being coupled with a second cable drum, a second cable pair, and the articulation unit of the endoscope, the first shaft is positioned within the second shaft; a brake disc having a central opening through which said second shaft extends, said brake disc being in physical contact with the second shaft; a stationary sleeve surrounding at least a portion of the second shaft; a brake base positioned below said brake disc, having a central opening through which said second shaft extends and comprising a first control edge; a brake lid positioned above said brake base and said brake disc, coupled to said brake base, having a central opening through which said second shaft extends and comprising a second control edge; a spring positioned between said brake base and said brake lid; a brake bushing positioned between said brake base and said brake lid and below said brake disc, having a central opening through which said second shaft extends and being movable vertically between first and second brake bushing positions; and a brake handle attached to said brake base for rotating said brake base and brake lid; wherein said brake bushing is movable from said first position to said second position by rotating said brake handle in a first rotational direction, causing said brake bushing to move upward and compress said brake disc against said brake lid, thereby locking the second shaft and braking the articulation unit in a predetermined direction, further wherein said brake bushing is movable from said second position into said first position by rotational motion of said brake handle in a second rotational direction opposite said first rotational direction, allowing the compressive force of said spring to push said brake bushing into said first position.

In one embodiment, the predetermined direction is an up/down (U/D) direction.

In one embodiment, the brake handle is of concentric design and positioned below the second operating knob for braking the articulation unit in a predetermined direction.

Optionally, in one embodiment, the brake base, lid, and bushing are supported by a housing surrounding the brake disc.

In one embodiment, the brake bushing comprises negative indentations on a surface for fitting into one or more positive indentations on a surface of the lid, compressing the brake bushing and the brake disc to the lid in the second position of the brake bushing. In one embodiment, in the first position of the brake bushing, the negative indentations on the surface of the brake bushing are not aligned with the positive indentations on the surface of the lid and the brake disc is freely movable.

The present specification also discloses an endoscope comprising a braking system for an articulation unit of the endoscope, said braking system comprising: a first shaft having a first end and a second end, the first end being coupled with a first operating knob, the second end being coupled with a first cable drum that is coupled with a first cable pair that is coupled with the articulation unit of the endoscope, at least a portion of the first shaft in proximity of the first operating knob being hollow; a second hollow shaft having a first end and a second end, the first end being coupled with a second operating knob, the second end being coupled with a second cable drum that is coupled with a second cable pair that is coupled with the articulation unit of the endoscope, the first shaft is positioned within the second shaft; a right/left movement controller unit comprising: a brake knob rotatable about its center axis; a first stationary sleeve arranged between the first and the second shafts; a first spring being supported by the first shaft in proximity to the first end; a pin extending into the hollow portion of the first shaft in a first pin position; and a brake body extending outwardly from said pin; wherein the pin is movable from the first pin position into a second pin position further into the hollow portion of the first shaft by rotational motion of said brake knob in a first brake knob rotational direction and compression of said first spring, wherein said brake body becomes pressed against said first stationary sleeve when said pin is in said second pin position, thereby locking said first shaft and braking the articulation unit in a first predetermined direction; further wherein said pin is movable from said second pin position into said first pin position by rotational motion of said brake knob in a second brake knob rotational direction opposite said first brake knob rotational direction, allowing the compressive force of said first spring to push said pin into said first pin position; and an up/down movement controller unit comprising: a brake disc having a central opening through which said second shaft extends, said brake disc being in physical contact with the second shaft; a second stationary sleeve surrounding at least a portion of the second shaft; a brake base positioned below said brake disc, having a central opening through which said second shaft extends and comprising a first control edge; a brake lid positioned above said brake base and said brake disc, coupled to said brake base, having a central opening through which said second shaft extends and comprising a second control edge; a second spring positioned between said brake base and said brake lid; a brake bushing positioned between said brake base and said brake lid and below said brake disc, having a central opening through which said second shaft extends and being movable vertically between first and second brake bushing positions; and a brake handle attached to said brake base for rotating said brake base and brake lid; wherein said brake bushing is movable from said first brake bushing position to said second brake bushing position by rotating said brake handle in a first brake handle rotational direction, causing said brake bushing to move upward and compress said brake disc against said brake lid, thereby locking the second shaft and braking the articulation unit in a second predetermined direction, further wherein said brake bushing is movable from said second brake bushing position into said first brake bushing position by rotational motion of said brake handle in a second brake handle rotational direction opposite said first brake handle rotational direction, allowing the compressive force of said second spring to push said brake bushing into said first brake bushing position.

Optionally, in one embodiment, the pin is held in the second pin position by a latching mechanism. In one embodiment, the latching mechanism comprises a control pin extending outwardly from said pin and a spiral groove having an upper portion and a lower portion with a recess formed in a wall of the first shaft. In one embodiment, the control pin is free to move within said spiral groove of said latching mechanism when said pin is in said first position and said control pin is latched into said recess of said lower portion of said spiral groove when said pin is in said second position.

Optionally, in one embodiment, a sealing element is provided between the first shaft and the first stationary sleeve.

In one embodiment, the brake bushing comprises negative indentations on a surface for fitting into one or more positive indentations on a surface of the lid, compressing the brake bushing and the brake disc to the lid in the second position of the brake bushing.

In one embodiment, the present specification describes a control unit providing a braking system for an articulation unit of an endoscope, said control unit comprising: a first shaft having a first end and a second end, the first end being coupled with a first operating knob, the second end being coupled with a first cable drum coupled with a first cable pair coupled with the articulation unit of the endoscope, at least a portion of the first shaft in proximity of the first operating knob being hollow; a second hollow shaft having a first end and a second end, the first end being coupled with a second operating knob, the second end being coupled with a second cable drum coupled with a second cable pair coupled with the articulation unit of the endoscope, the first shaft penetrating the second shaft; a first stationary sleeve arranged between the first and the second shafts; a brake body being radially displaceable in at least one radial opening made in a wall of the hollow portion of the first shaft; a spring being supported by the first shaft in proximity to the first end; and a pin extending into the hollow portion of the first shaft in a first position, the pin being movable from the first position into a second position out of the hollow portion of the first shaft by a force of the spring, the pin in the second position pushing the brake body out of the radial opening of the first shaft, the brake body being pressed against the first stationary sleeve locking the first shaft, thereby braking the articulation unit in a predetermined direction. In an embodiment, the control unit causes braking of the articulation unit in a right/left (R/L) direction.

In an embodiment, the pin is mounted in the first shaft for countering the force of the spring.

In an embodiment, the pin is moved from the first position into the second position by one of a translation and a rotation motion.

In an embodiment, the control unit further comprises a brake knob of concentric design positioned above the first operating knob for braking the articulation unit in a predetermined direction.

In an embodiment, the pin is held in the first position by a latching device comprising a control pin extending radially from the pin, the control pin being receivable in a spiral groove formed in a wall of the first shaft. In an embodiment, a sealing element is provided between the first shaft and the first stationary sleeve.

In another embodiment, the present specification provides a control unit providing a braking system for an articulation unit of an endoscope, said control unit comprising: a first shaft having a first end and a second end, the first end being coupled with a first operating knob, the second end being coupled with a first cable drum coupled with a first cable pair coupled with the articulation unit of the endoscope, at least a portion of the first shaft in proximity of the first operating knob being hollow; a second hollow shaft having a first end and a second end, the first end being coupled with a second operating knob, the second end being coupled with a second cable drum coupled with a second cable pair coupled with the articulation unit of the endoscope, the first shaft penetrating the second shaft; a brake disc coupled with the second shaft; a stationary sleeve surrounding at least a portion of the second shaft, the stationary sleeve supporting a spring on a first control edge; a brake element comprising a second control edge being supported by the first control edge of the stationary sleeve in a first position for countering a force of the spring, the spring creating frictional force between the brake disc and the brake element, said brake element being movable from the first position into a second position exerting pressure on the brake disc locking the second shaft, thereby braking the articulation unit in a predetermined direction. In an embodiment, the control unit causes braking of the articulation unit in an up/down (U/D) direction.

In an embodiment, the control unit further comprises a brake knob of concentric design positioned above the second operating knob for braking the articulation unit in a predetermined direction.

In an embodiment, the brake element is supported by a housing surrounding the brake disc.

In an embodiment, the brake element comprises at least a brake bushing, a brake drum and a lid, the brake disc being positioned between the brake bushing and the lid, the brake bushing comprising negative indentations on a surface for fitting into one or more positive indentations on a surface of the lid compressing the brake bushing and the brake disc to the lid in the second position of the brake element. In the first position of the brake element, the negative indentations on the surface of the brake bushing are not aligned with the positive indentations on the surface of the lid and the brake disc is freely movable.

In an embodiment, the control unit further comprises a brake handle being rotated from a first position to a second position for causing the brake element to move from the first position to the second position.

The aforementioned and other embodiments of the present specification shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

In one embodiment, the present specification discloses an endoscope having a tip section equipped with multiple viewing elements. In one embodiment, a braking system for fixing a tip of the endoscope in a desired position is provided.

In an embodiment, the endoscope of the present specification comprises a handle from which an elongated shaft emerges. The elongated shaft terminates with a tip section which is turnable by way of a bending section. In an embodiment, the endoscope comprises a plurality of steering cable eyes, positioned on the internal walls of the bending section. Through these eyes, steering cables are threaded to enable the maneuvering of the bending section comprising the tip of the endoscope. In an embodiment, the handle is used for maneuvering the elongated shaft within a body cavity by means of one or more knobs which control the bending section. In an embodiment, the braking system of the present specification ensures that a directional readjustment of right and left (or up and down) movement of the endoscope tip is possible. Further, the movement of the endoscope tip in the right-left direction or the up-down direction can be arrested using the braking system.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
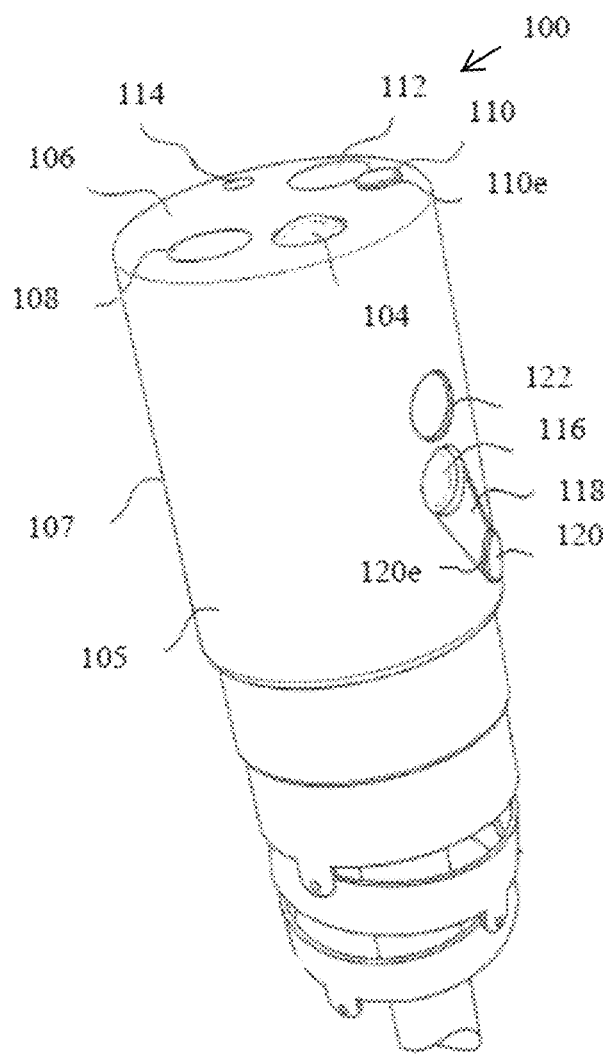
FIG. 1 illustrates a perspective view of a distal end of a multi-viewing elements endoscope, in accordance with an embodiment of the present specification.

Referring to FIG. 1, a perspective view of a distal end of a multi-viewing elements endoscope 100, in accordance with an embodiment of the present specification, is shown. A tip section 107 of the endoscope 100 includes therein a front-pointing viewing element 104 for capturing images through a hole in a distal end surface 106 of the tip section.

A discrete front illuminator 108, which is, in an embodiment, a light-emitting diode (LED), is associated with front-pointing viewing element 104 and used for illuminating its field of view through another hole in distal end surface 106.

A front fluid injector 110 is used for cleaning at least one of front-pointing viewing element 104 and discrete front illuminator 108. In one embodiment, front fluid injector 110 further includes a nozzle 110e for directing fluid toward at least one of front-pointing viewing element 104 and discrete front illuminator 108. Distal end surface 106 further includes a hole defining a working channel 112, which may be a hollow tube configured for insertion of a surgical tool to operate on various tissues. A pathway fluid injector 114, defined by another hole in distal end surface 106, is used for inflating and/or cleaning the body cavity into which endoscope 100 is inserted.

Tip section 107 further comprises therein a side-pointing viewing element 116 used for capturing images through a hole in a cylindrical surface 105 of the tip section 107. A discrete side illuminator 122, which is optionally similar to discrete front illuminator 108, in one embodiment, is associated with side-pointing viewing element 116 and used for illuminating its field of view through another hole in cylindrical surface 105.

A side fluid injector 120 is used for cleaning at least one of side-pointing viewing element 116 and discrete side illuminator 122. In one embodiment, side fluid injector 120 further includes a nozzle 120e for directing fluid toward at least one of side-pointing viewing element 116 and discrete side illuminator 122. In order to prevent tissue damage when cylindrical surface 105 of tip section 107 contacts a side wall of the body cavity, side fluid injector 120 and side-pointing viewing element 116, in one embodiment, are located in a depression 118 in the cylindrical surface 105. In an alternative configuration (not shown), one or more discrete side illuminators may also be included in the depression, so that fluid injected from the side fluid injector reaches them. In yet another configuration (not shown), a side-pointing viewing element, one or more side illuminators and a side fluid injector may not be located in a depression, but rather be on essentially the same level as the cylindrical surface of the tip section. Further, in other embodiments, another side-pointing viewing element, one or more additional side illuminators, and another side fluid injector are positioned, within a depression or on the surface level, on another side or on the opposite side of the cylindrical surface from side pointing viewing element 116.

Figure 2:
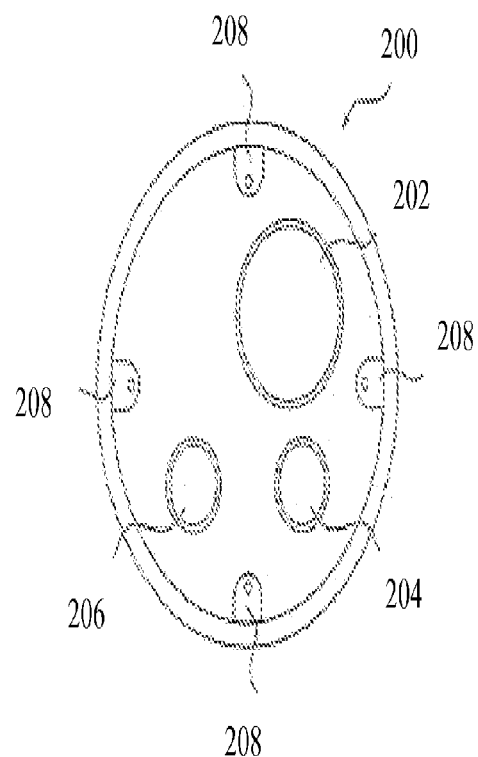
FIG. 2 illustrates a cross-sectional view of a bending section of a multi-viewing elements endoscope, in accordance with an embodiment of the present specification.

Reference is now made to FIG. 2, which shows a cross-sectional view of a bending section 200 of a multi-viewing elements endoscope, such as multi-viewing elements endoscope 100 of FIG. 1. A plurality of steering cable eyes, such as four eyes 208, are positioned on the internal walls of bending section 200. Through these eyes 208, steering cables are threaded to enable the maneuvering of bending section 200.

Bending section 200, in an embodiment, comprises a working channel 202, through which surgical tools are inserted, a fluid channel 206, through which fluids and/or liquids are infused, and an electrical channel 204 with a plurality of electrical cables threaded through it, for transmitting video signals from the viewing elements and for supplying power to the viewing elements and the discrete illuminators.

Figure 3:
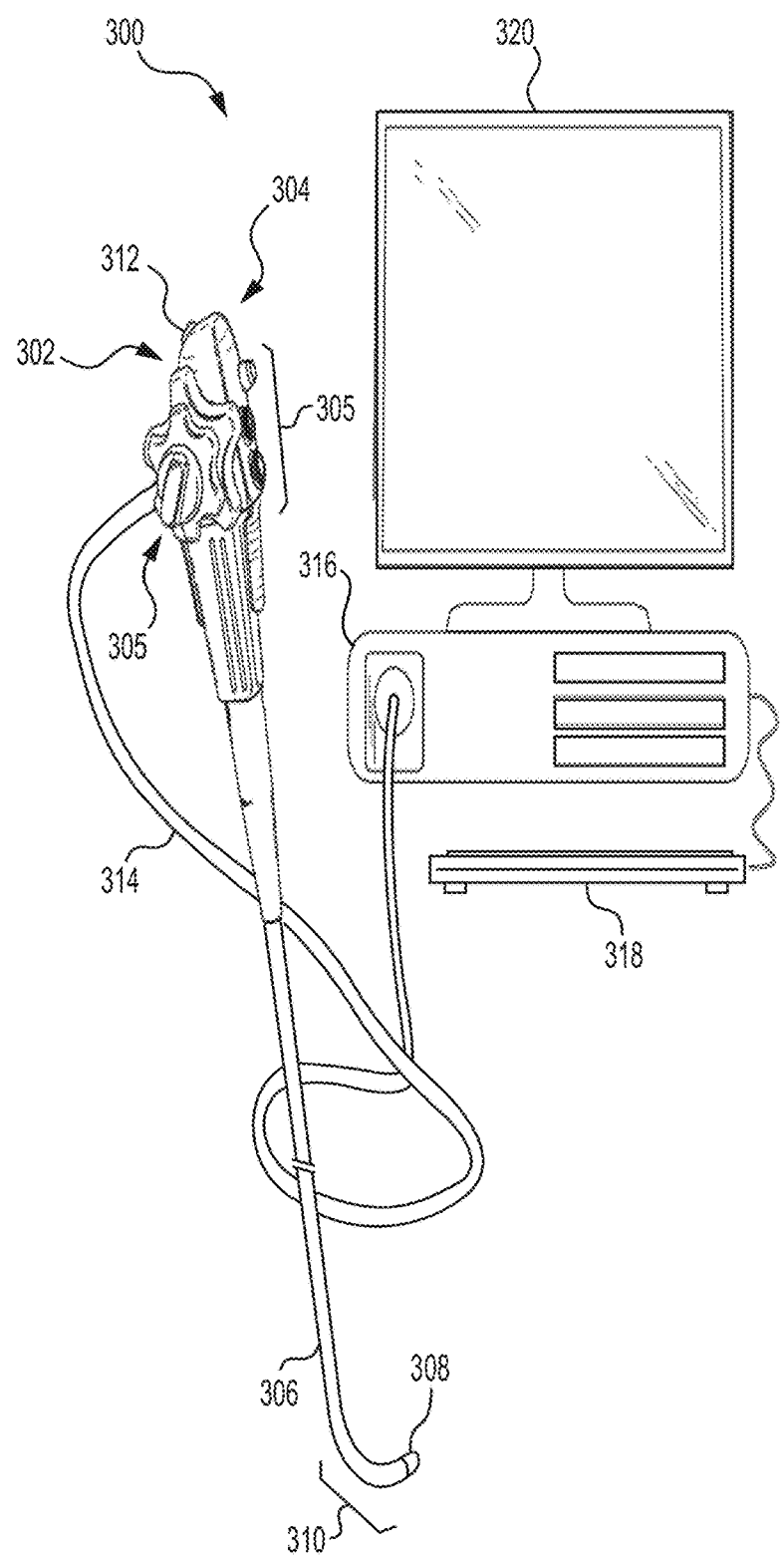
FIG. 3 illustrates a multi-viewing elements endoscopy system, in accordance with an embodiment of the present specification.

Reference is now made to FIG. 3, which shows a multi-viewing elements endoscopy system 300. System 300 comprises a multi-viewing elements endoscope 302. Multi-viewing elements endoscope 302 comprises a handle 304 from which an elongated shaft 306 emerges. Elongated shaft 306 terminates with a tip section 308 which is turnable by way of a bending section 310. In an embodiment, handle 304 is used for maneuvering elongated shaft 306 within a body cavity; the handle comprises one or more knobs and/or switches 305 which control bending section 310 as well as functions such as fluid injection and suction. Handle 304 further comprises a working channel opening 312 through which surgical tools are inserted.

A utility cable 314 connects handle 304 and a controller 316. Utility cable 314 comprises therein one or more fluid channels and one or more electrical channels. The electrical channel(s) comprises at least one data cable for receiving video signals from the front and side-pointing viewing elements, as well as at least one power cable for providing electrical power to the viewing elements and to the discrete illuminators.

In an embodiment, one or more input devices, such as a keyboard 318, is connected to controller 316 for the purpose of human interaction with the controller 316. Also in an embodiment, a display 320 is connected to controller 316 and configured to display images and/or video streams received from the viewing elements of multi-viewing elements endoscope 302.

Figure 4A:
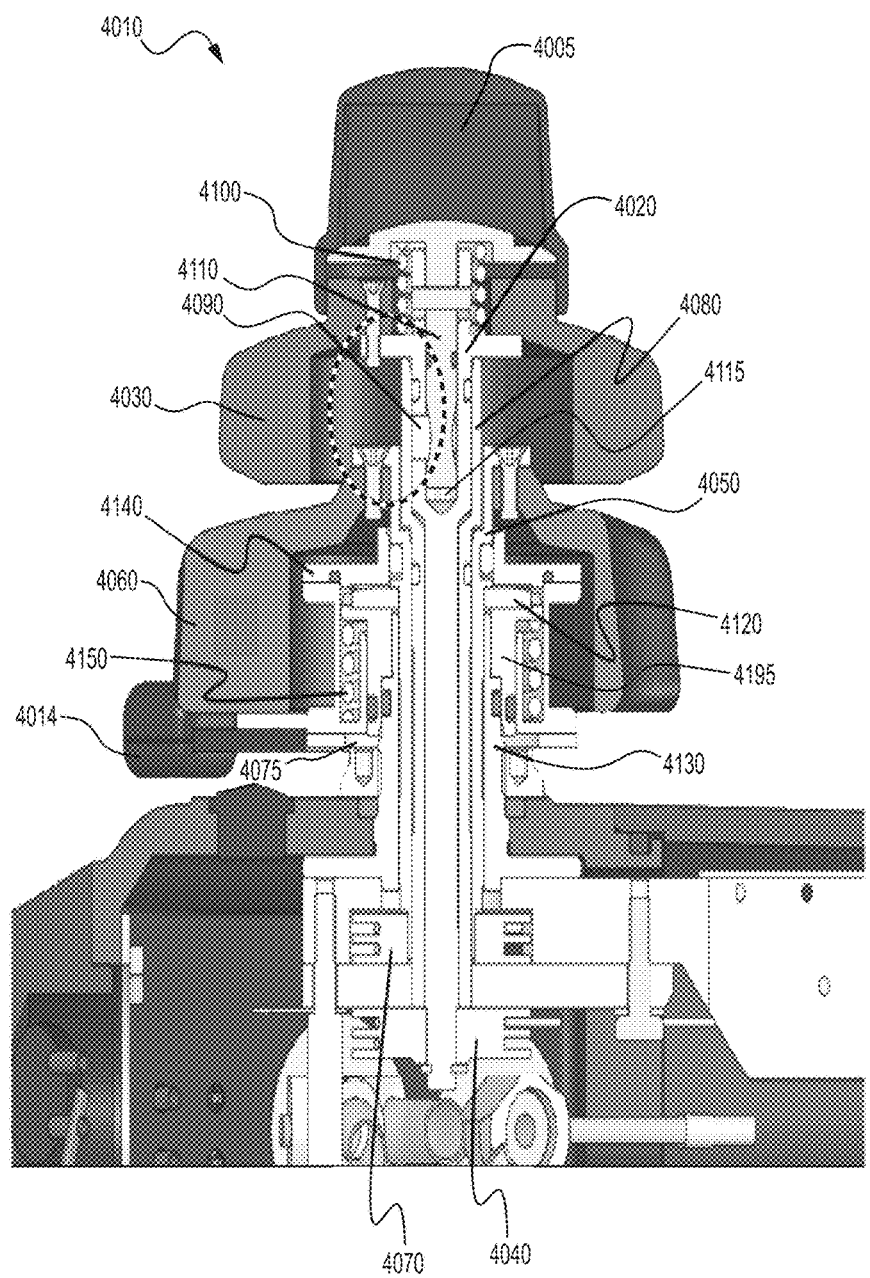
FIG. 4A illustrates a cross-sectional view of a handle of an endoscope comprising a braking system, in accordance with an embodiment of the present specification.

FIG. 4A shows a cross section of an exemplary embodiment of a control unit 4010 for an endoscope. The control unit 4010 is incorporated into the handle of the endoscope. This example exhibits a locking or braking means for the movements right-left (R-L) as well as up-down (U-D). It would be appreciated that the operating elements are of concentric design and thus permit simple and intuitive operation.

The control unit 4010 comprises a first shaft 4020 that is connected at its proximal end to a first operating knob 4030. At its distal end, the shaft 4020 is connected to a first cable drum 4040. The cable drum 4040 is attached to a first cable pair (not shown), which is further attached with an articulation unit (not shown) of the endoscope. As explained earlier, the deflection of the articulation unit can be controlled for manoeuvring and fixing the position of the endoscope tip. In an embodiment, the first cable pair connected to the cable drum 4040 is arranged for moving the articulation unit in the direction R-L or U-D. If, for example, the first cable pair is arranged to provide a R-L movement, the corresponding movement of the articulation unit can be triggered by moving the first operating knob 4030.

In one embodiment, at least a part of the first shaft 4020 is designed as a hollow shaft in the area of the first operating knob 4030. In one embodiment, at least one radial opening is provided in the wall of the hollow shaft, which is occupied by a brake body 4090. The brake body 4090 can be shifted radially in the opening. In one embodiment, a plurality of brake bodies 4090 is provided.

In one embodiment, to achieve locking of the first shaft 4020, a brake knob 4005 of concentric design is provided above the first operating knob 4030. The brake knob 4005 is rotatable about its center axis. The braking system further comprises a first pin 4110 that extends into the hollow section of the first shaft 4020. The first pin 4110 is mounted to counter the force of a first spring 4100 that is supported on the first shaft 4020. Here the components are arranged relative to each other such that the first pin 4110 can be forced out of the hollow-shaft section by means of the first spring 4100. The first pin 4110 further exhibits a tapered section 4115 that receives the brake body/bodies 4090 in a first position. This first position of the brake body 4090 is shown in FIG. 4A.

The first pin 4110 can be moved from this first position into a second position by means of translation and/or rotation, counter to the force of the first spring 4100 that is supported on the first shaft 4020. When moved from the first position to the second position, the first pin 4110 acts on the brake body 4090 in such a manner that it is partly forced downward through the opening of the shaft 4020 and is pressed against a first stationary sleeve 4080 that is arranged between the first shaft 4020 and a second shaft 4050.

This frictional connection between the brake body 4090 and the first stationary sleeve 4080 locks the first shaft 4020, thus braking the articulation unit in the R-L direction. It would be appreciated that the setting of the articulation unit relative to the R-L direction can be readjusted or finally adjusted after braking by overcoming the friction of the brake body 4090 and the first stationary sleeve 4080, wherein the level of the frictional force is predetermined by the pretension of the first spring 4100 that puts pressure on the first pin 4110 in an upward direction out of the hollow-shaft section.

In one embodiment, the first pin 4110 is held in the first position in a latching device that has to be overcome initially for the first pin 4110 to be brought into the second position. This allows the user operating the control unit to receive a touch-feedback on tightening and releasing the brake.

Figure 4B:
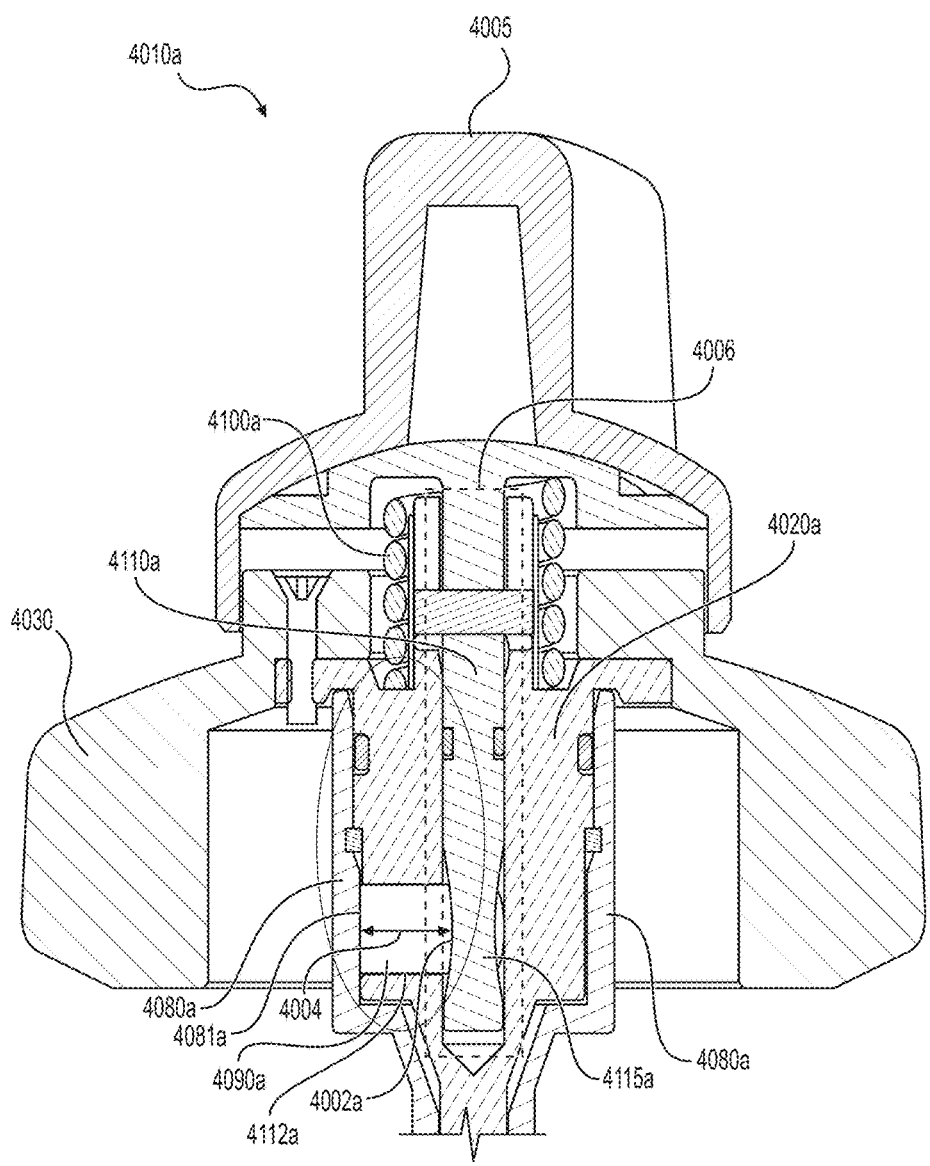
FIG. 4B illustrates a close-up cross-sectional view of an alternative arrangement of a first shaft and a first stationary sleeve within a control unit, in accordance with an embodiment of the present specification.
Figure 4C:
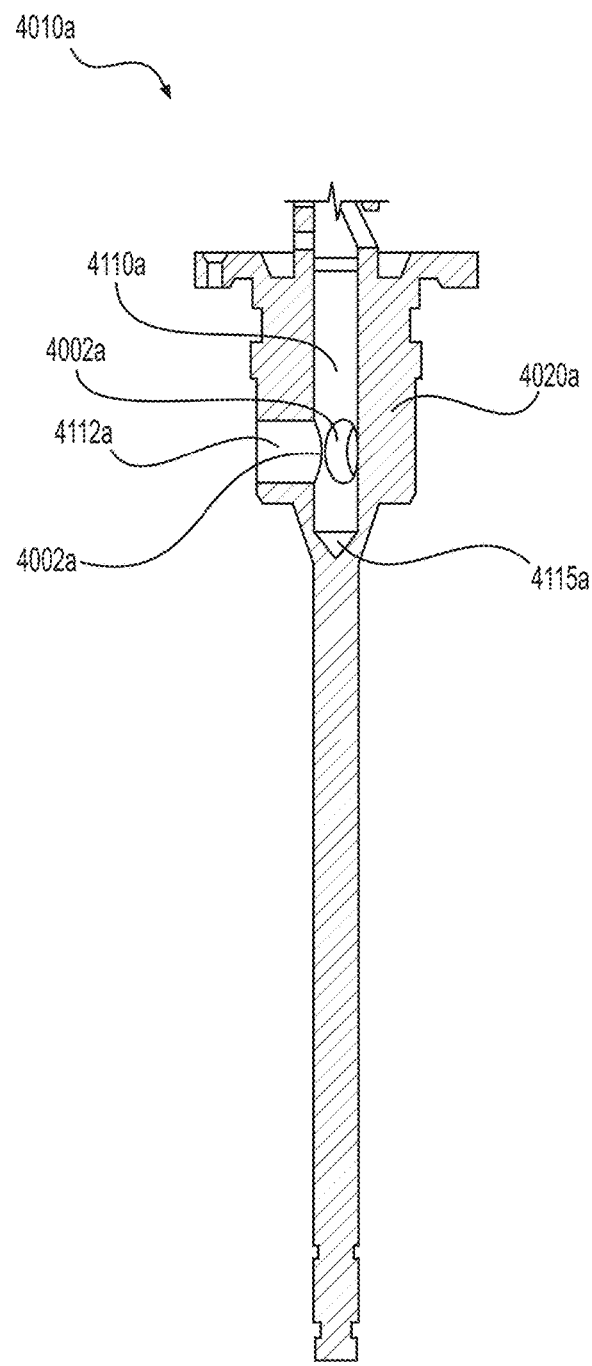
FIG. 4C illustrates an enlarged cross-sectional view of the first shaft within the control unit depicted in FIG. 4B.

FIG. 4B illustrates a close-up cross-sectional view of an alternative arrangement of a first shaft 4020a and a first stationary sleeve 4080a within a control unit 4010a, in accordance with an embodiment of the present specification. FIG. 4C illustrates an expanded cross-sectional view of the first shaft 4020a within the control unit 4010a depicted in FIG. 4B. Referring now to FIGS. 4B and 4C simultaneously, a first shaft 4020a and a first stationary sleeve 4080a arrangement are shown within control unit 4010a. In an embodiment, a proximal portion of first shaft 4020a includes a space 4006. In some embodiments, space 4006 is configured to receive first pin 4110a. In various embodiments, the first pin 4110a comprises an elongated member having an external surface area configured to be slidably received within space 4006. First pin 4110a is sized such that it is capable of rotating within space 4006. In one embodiment, first pin 4110a further comprises a tapered section 4115a that includes one or more pin openings 4002a configured to receive brake body/bodies 4090a in a first position. In another embodiment (not shown), the section of the first pin including one or more pin openings is not tapered.

This first position of the brake body 4090a is shown in FIG. 4B, wherein the braking mechanism is engaged. In one embodiment, at least one radial shaft opening 4112a is provided in the first shaft 4020a, such that radial shaft opening 4112a is aligned with pin opening 4002a of pin 4110a. In various embodiments, radial shaft opening 4112a is elongated and cylindrically shaped. In various embodiments, the brake body 4090a comprises an elongate member sized to fit within said radial shaft opening 4112a. Brake body 4090a may be perpendicularly aligned to the first shaft 4020a and first pin 4110a. Pin opening 4002a may support the alignment of brake body 4090a such that brake body 4090a extends perpendicularly outwards from the first pin 4110a. Brake body 4090a can be shifted longitudinally and radially relative to the first stationary sleeve 4080a.

Rotational movement of the brake knob 4005a in a first direction is translated into distal movement of the first pin 4110a into space 4006, resulting in the brake body/bodies 4090a sliding within said radial shaft opening 4112a and said pin opening 4002a and shifting distally within said space 4006. As the brake bodies 4090a shift distally, they come into contact with an inner surface 4081a of said first stationary sleeve 4080a, enabling the locking mechanism. Rotational movement of the brake knob 4005a in a second direction opposite said first direction moves allows the compression force of spring 4100a to push said first pin 4110a in a proximal direction, resulting in sliding movement and proximal movement of said brake body/bodies 4090a away from said inner surface 4081a, eliminating the contact between said brake body/bodies 4090a and said sleeve 4080a, thus disabling the braking mechanism. Though sleeve 4080a is depicted in FIG. 4B as having a varying wall thickness, other embodiments are envisioned wherein sleeve 4080a has a consistent wall thickness throughout its length, and wall thickness is not intended to contribute to the functioning of the braking mechanism.

Figure 4D:
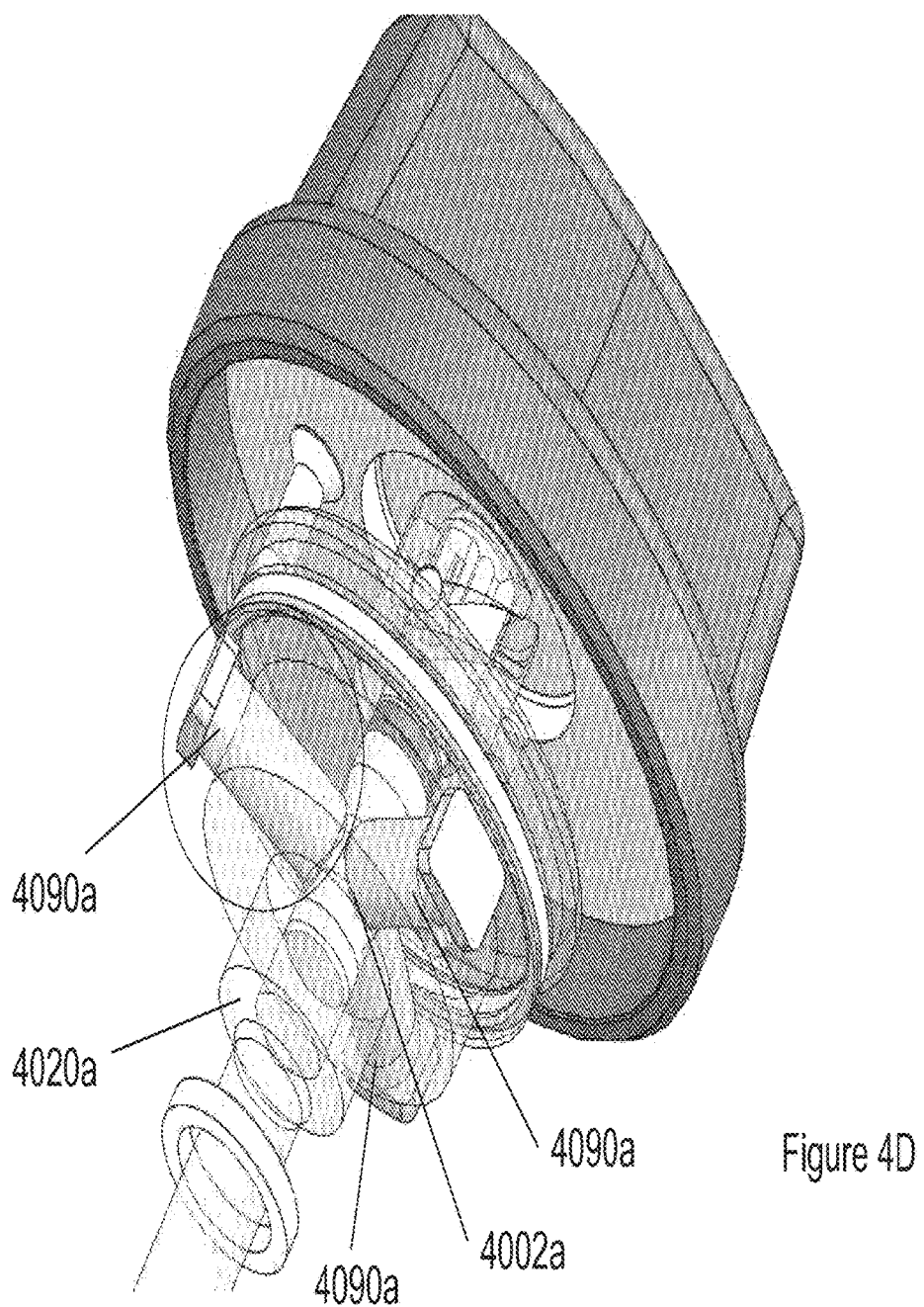
FIG. 4D illustrates a perspective view of the respective positions of three brake bodies within a first shaft, in accordance with some embodiments of the present specification.

In one embodiment, a plurality of brake bodies 4090a is provided, each through a different shaft opening 4112a and pin opening 4002a. Referring to FIG. 4D, in an embodiment having three brake bodies 4090a, the central axis of any one of the three brake bodies 4090a is positioned approximately 120 degrees from the central axis of the adjacent brake body 4090a. FIG. 4D illustrates a perspective view of the respective positions of three brake bodies 4090a within first shaft 4020a, in accordance with some embodiments of the specification. Elongated brake bodies 4090a extend radially outwards through pin openings 4002a in the wall of first shaft 4020a. In other embodiments, the control unit includes two, three, or more brake bodies.

In the embodiments depicted in FIGS. 4B through 4D, brake body 4090a is slightly elongated as compared to the brake body 4090 depicted in FIG. 4A. In addition, a width of the first shaft 4020a is increased relative to a width of shaft 4020 of FIG. 4A to accommodate the longer brake bodies 4090a. An elongated length 4004 of brake body 4090a provides increased torque for braking. In embodiments, brake body 4090 may have a length in the range of 3-4 millimeters (mm). In various embodiments, elongated brake body 4090a may have a length between 4 to 10 mm, between 7 to 8 mm, or any other length in the range of 4 to 10 mm. Radial opening 4002a within the wall of first shaft 4020a extends along a thickness 4004 of wall of first shaft 4020a. In embodiments, thickness 4004 must be sufficient to support the length of brake body 4090a. Therefore, thickness 4004 may be similar to length of brake body 4090a.

Figure 5A:
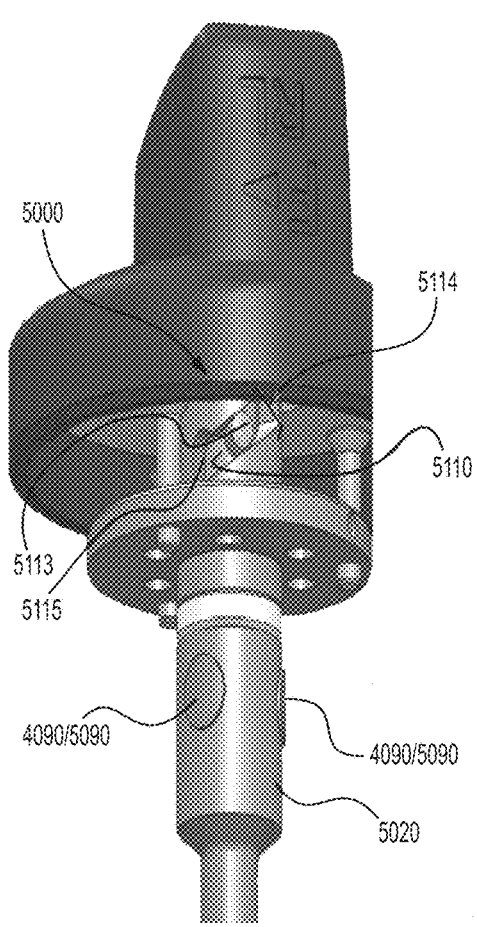
FIG. 5A illustrates an embodiment of a latching mechanism incorporated in an endoscope braking system facilitating freewheeling and arrest operation for controlling the right-left movement of the endoscope tip, depicting a control pin in a first position.
Figure 5B:
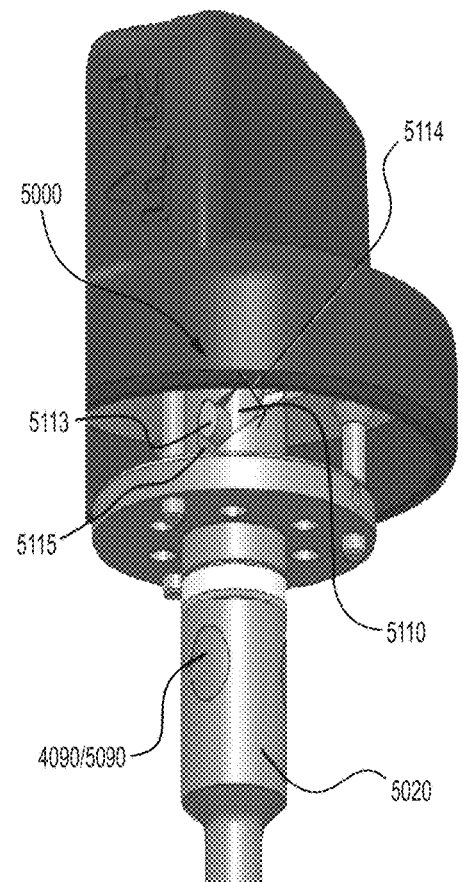
FIG. 5B illustrates the embodiment of the latching mechanism incorporated in an endoscope braking system of FIG. 5A, depicting the control pin in a second position.

FIGS. 5A and 5B illustrate a latching mechanism 5000 incorporated in the endoscope braking system for facilitating freewheeling and arrest operation for controlling the right-left movement of the endoscope tip, in accordance with an embodiment of the present specification. In one embodiment, as is shown in FIGS. 5A and 5B, holding the first pin 5110 in the latching mechanism can be achieved by having a control pin 5113 that extends outwardly from an outer surface of the first pin 5110. The control pin 5113 is received in a control section or groove 5114 that extends in a spiral form from a lower portion to an upper portion in the shaft 5020 and at the same time effects a rotation and a shift. Basically, the control section 5114 is formed as a guide introduced into the wall of the shaft 5020. A recess 5115 is formed in the lower portion of the guide into which the control pin 5113 can latch on account of the force of the first spring and be pressed out again therefrom. FIGS. 5A and 5B illustrate a first and a second position of the control pin 5113 within the control section 5114, respectively. Referring to FIG. 5A, the control pin 5113 is in the first position and free to move within the guide of the control section 5114. When the control pin 5113 is in the first position, the first spring (4100 in FIG. 4) is relaxed, the shaft 5020 does not press against the first stationary sleeve (4080 in FIG. 4), and R-L braking is not engaged. Referring to FIG. 5B, the control pin 5113 is in the second position, engaged within the recess 5115 of the control section 5114. When the control pin 5113 is in the second position, the first spring (4100 in FIG. 4) is compressed, the shaft 5020 is pressed against the first stationary sleeve (4080 in FIG. 4), and R-L braking is engaged.

Referring back to FIG. 4, the control unit 4010 exhibits a second shaft 4050 that is connected at its proximal end to a second operating knob 4060 and at its distal end to a second cable drum 4070 for attaching a second cable pair (not shown) that is attached with the articulation unit (not shown). The cable pair that is connected to the second cable drum 4070 is designed to move the articulation unit in the direction U-D, such that a U-D movement of the articulation unit can be effected by moving the second operating knob 4060.

In one embodiment, the second shaft 4050 is advantageously designed as a hollow shaft and the first shaft 4020/4020a is positioned within, or penetrates, the second shaft 4050, providing a concentric design. In various embodiments, a compact control unit is obtained due to this concentric design.

The second operating knob 4060 exhibits a braking device wherein the second shaft 4050 is in contact with a brake disc 4120. In one embodiment, the brake disc 4120 can be fixed up to a predetermined desired degree by means of a frictional connection.

In one embodiment, at least a section of the second shaft 4050 is surrounded by a second stationary sleeve 4130 and a brake base 4075 (also seen in FIGS. 6A and 6B) that exhibits a first control edge. Further, a brake lid 4140 is provided that is mounted to counter the force of a second spring 4150 that is supported about the second stationary sleeve 4130, and exhibits a second control edge that supports the second spring 4150 between itself and the first control edge of the base 4075. A brake bushing 4195 is also positioned between the brake lid 4140 and brake base 4075 and can be brought from a first position into a second position by means of translation and/or rotation counter to the force of the spring 4150 that is supported on the second stationary sleeve 4130. In one embodiment, said translation and/or rotation is effectuated by rotation of a brake handle 4014. On account of the geometry resulting from the control edges, the brake bushing 4195 in the first position does not produce any effect on the brake disc 4120, while in the second position, the brake bushing 4195 exerts pressure on the brake disc 4120 and thus fixes the position of the second shaft 4050.

The braking process is particularly effective if the brake disc 4120 is clamped in between the brake lid 4140 and the second stationary sleeve 4130, or if a further brake element is connected to it.

This frictional connection between the brake disc 4120 and the brake lid 4140 and brake bushing 4195 locks the second shaft 4050 and thus the setting of the articulation unit in the U-D direction. Here, too, the level of the frictional force is predetermined by the pretension of the second spring 4150 that presses the brake bushing 4195 against the brake disc 4120.

In one embodiment, a sealing element exists between the first shaft 4020/4020a and the first stationary sleeve 4080/4080a. Also, since the brake lid 4140 is part of a housing that surrounds the brake disc 4120, it is sealed using sealing means, so that both locking devices are protected against the ingress of moisture.

This produces a control unit 4010 that is simple in design and watertight, and maintains a haptically recognisable separation between freewheeling and locking and is easy to operate.

Figures 6A, 6B:
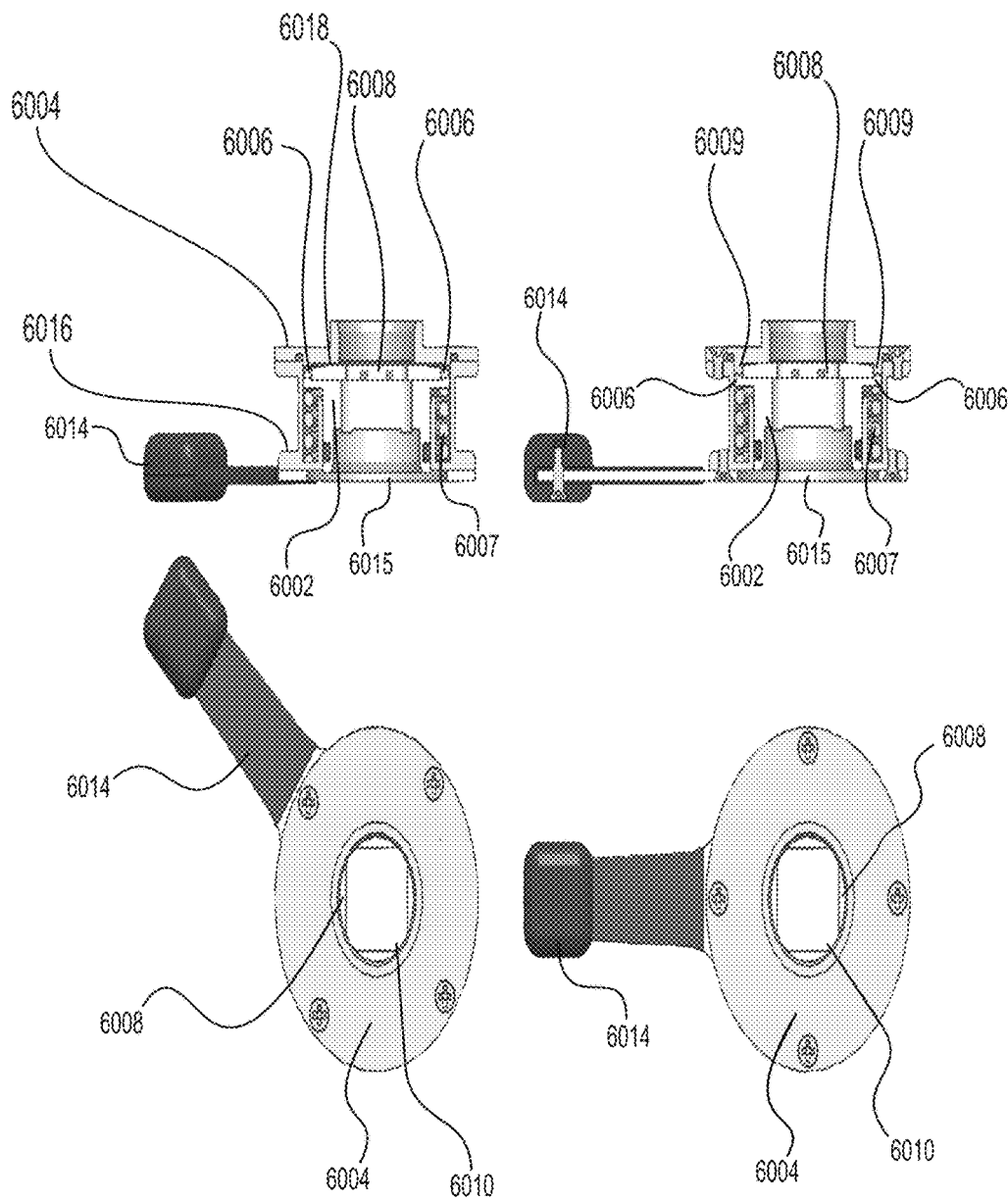
FIG. 6A illustrates cross-sectional side and top down views of one embodiment of a portion of a braking system for controlling an up-down (U-D) movement of an endoscope tip, depicting a brake handle in a first position.
FIG. 6B illustrates cross-sectional side and top down views of the embodiment of a portion of a braking system for controlling an up-down (U-D) movement of an endoscope tip of FIG. 6A, depicting the brake handle in a second position.

In various embodiments, five components, namely, a brake bushing, a brake drum, a brake disc, a second compression spring and a lid are responsible for causing a braking action arresting a movement of the endoscope tip in a U-D direction. FIGS. 6A and 6B illustrate cross-sectional side views and top down views of a portion of the braking system of an endoscope causing a freewheeling and arrest operation of the endoscope tip in an up-down (U-D) direction, in accordance with an embodiment of the present specification.

As illustrated in FIGS. 6A and 6B, all components of the braking system are arranged in parallel. A brake bushing 6002 and a lid 6004 are shaped with negative indentations 6006 and positive indentations, or protrusions 6009, respectively. A brake disc 6008 is positioned between the brake bushing 6002 and the lid 6004 and all the three parts are compressed by a second compression spring 6007.

In a freewheeling position, as seen in FIG. 6A, the negative indentations 6006 of the brake bushing 6002 and the protrusions 6009 of the lid 6004 are positioned away from one another, creating a small gap 6018 and allowing the brake disc 6008 to move freely. A square head (not shown) connects the brake disc 6008 to a U-D control wheel, which enables the U-D movement of the endoscope tip. The square head is part of the U-D control wheel which fits into a square hole 6010 in the brake disc 6008, operatively coupling the U-D control wheel and the brake disc 6008.

A braking effect for fixing the endoscope tip position in a desired location is triggered by using a brake handle 6014. In an embodiment, the turning of the handle 6014 between two snapping positions (freewheeling and braking positions) is limited to an angle of 40°. FIG. 6B illustrates the up-down braking system with the brake engaged. The brake handle 6014 includes a base 6015 which is screwed on to a brake drum 6016 and changes the position of the brake drum 6016 and lid 6004 relative to the brake bushing 6002 when rotated counter-clockwise. The protrusions 6009 slide into the negative indentations 6006, the gap 6018 is eliminated and the brake bushing 6002 is compressed up to the lid 6004 by spring power of the second compression spring 6007. As illustrated in FIG. 6A, a small gap 6018 between the brake disc 6008 and the lid 6004 is maintained during the freewheeling operation, allowing the brake disc 6008 to move freely. In FIG. 6B, the gap 6018 is eliminated and the brake disc 6008 is fixed to the lid 6004 when the braking effect is activated.

Figure 6C:
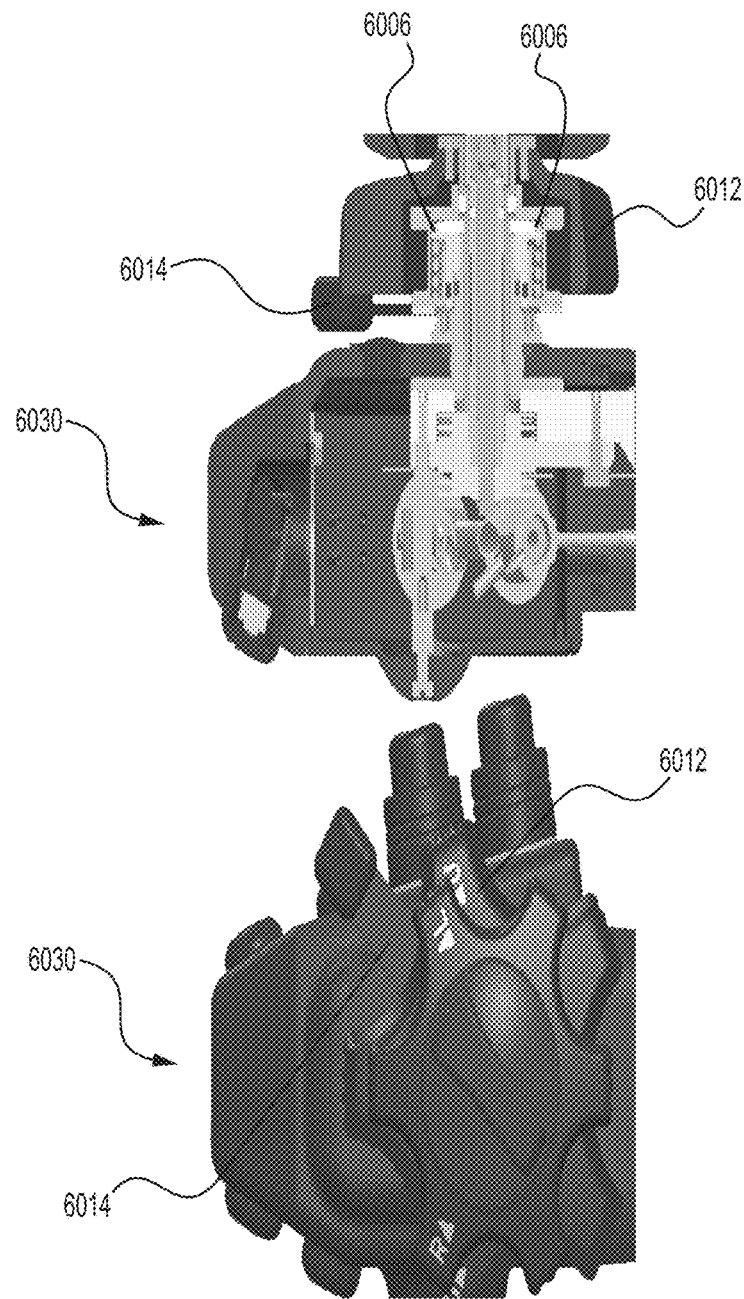
FIG. 6C illustrates cross-sectional side and top down views of one embodiment of a handle of an endoscope, depicting an up-down (U-D) braking system disengaged; and, FIG. 6D illustrates cross-sectional side and top down views of the embodiment of the handle of an endoscope of FIG. 6C, depicting the up-down (U-D) braking system engaged.

FIG. 6C illustrates a cross-sectional side view and a top down view of a handle 6030 of an endoscope depicting one embodiment of an up-down (U-D) braking system disengaged. The brake handle 6014 is in its disengaged position and the protrusions of the lid are not aligned with the negative indentations 6006 of the bushing. In this configuration, the up-down control wheel 6012 is free to move.

Figure 6D:
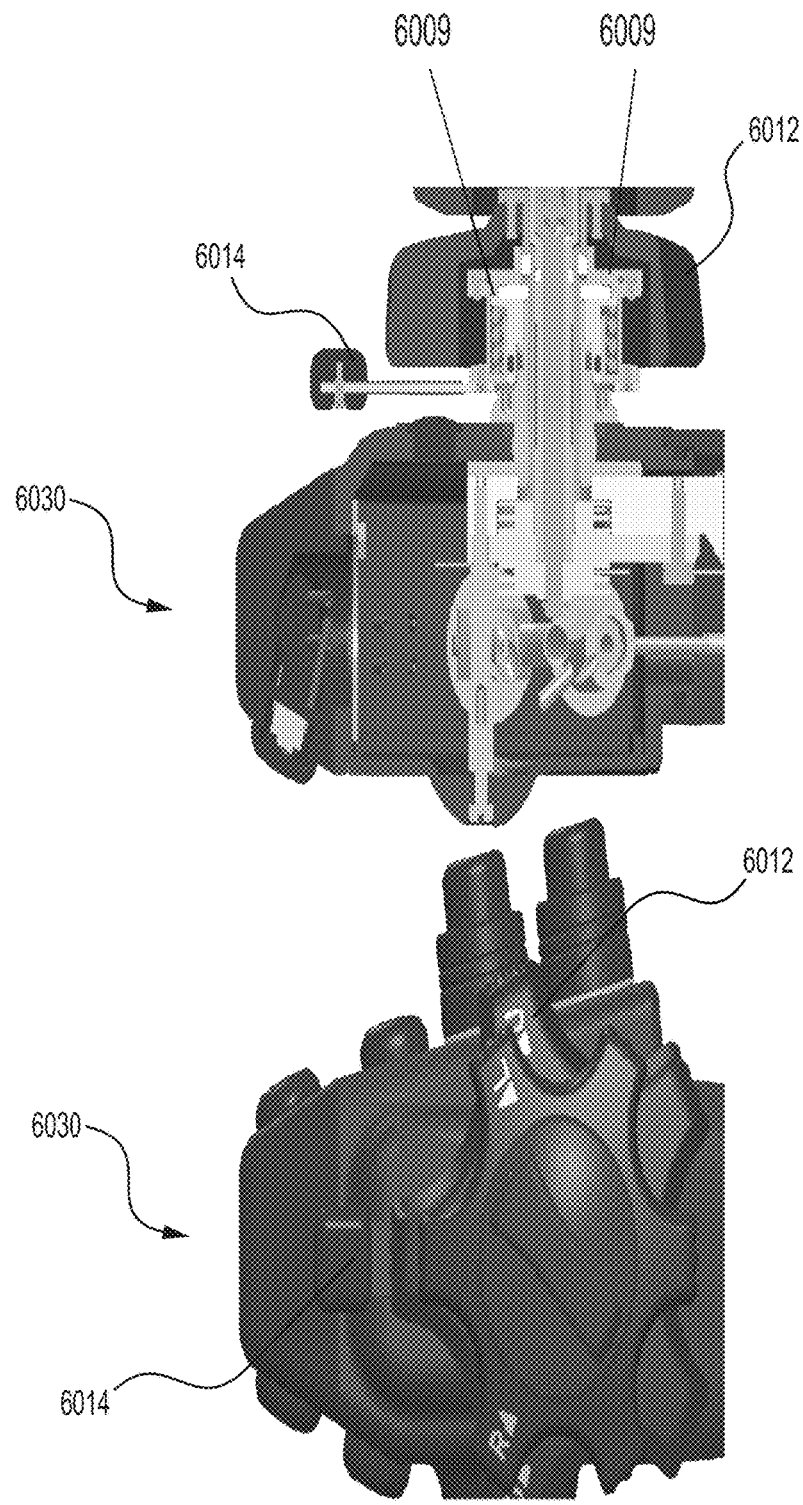

FIG. 6D illustrates a cross-sectional side view and a top down view of a handle 6030 of an endoscope depicting one embodiment of an up-down (U-D) braking system engaged. The brake handle 6014 has been rotated into its engaged position and the protrusions 6009 of the lid are snapped into the indentations of the bushing. In this configuration, the up-down control wheel 6012 is fixed.

After the brake is actuated, it is still possible to move the U-D control wheel 6012 with slightly increased force and thus to bring the tip of a distal end of the endoscope into a desired position. In an embodiment, in order to deactivate the braking effect and achieve the freewheeling operation, the U-D knob is rotated in a clockwise direction through a 40 degree angle and a force is applied, thereby causing the protrusions to snap out of the negative indentations.

Hence, the present specification provides a braking system for use with an endoscope for maneuvering the tip of a distal end of an endoscope insertion tube. The endoscope tip may be easily moved in an up down as well as right left direction by using the braking system of the present specification. Further, the braking system enables smooth transition between smooth directional readjustment of right and left (or up and down) movement of the insertion tube tip after applying brake for fixing the end position. The braking system provided is a watertight system that provides a complete separation between freewheeling and locking operations.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive.

We claim:

1. An endoscope system comprising:
a first articulation actuator;
a first shaft coupled to the first articulation actuator;
a first sleeve, wherein the first shaft is received in the first sleeve; and
a braking system, comprising:
a first braking actuator, wherein the first braking actuator includes a pin received in the first shaft,
at least one brake body, wherein the at least one brake body is received in the first shaft, and wherein the at least one brake body extends radially outward from said pin;
wherein the pin and the at least one brake body are engaged, such that movement of the pin, via actuation of the first braking actuator, is configured to move the at least one brake body between a retracted position and an extended position,
wherein the at least one brake body presses against the first sleeve when the at least on brake body is in the extended position, and
wherein the at least one brake body is retracted away from the first sleeve when the at least one brake body is in the retracted position.

2. The endoscope system of claim 1, wherein the first braking actuator includes a protrusion, wherein the protrusion is received in a groove of the first shaft, and wherein movement of the protrusion in the groove moves the first braking actuator in at least one of a proximal direction or a distal direction.

3. The endoscope system of claim 1, further including a biasing member configured to bias the first braking actuator to move from an actuated position, where the brake body is in the extended position, to a rest position, where the brake body is in the retracted position.

4. The endoscope system of claim 1, further comprising:
a second articulation actuator;
a second shaft coupled to the second articulation actuator, wherein the first shaft is received by the second shaft, and
a second sleeve, wherein the second shaft is received in the second sleeve,
wherein the braking system further comprises:
a braking lid, wherein said second shaft is received in said braking lid,
a braking disc configured to move between an extended position, wherein the braking disc is engaged with the braking lid, and a retracted position, wherein the braking disc is disengaged from the braking lid,
a braking bushing, wherein said braking bushing receives said second shaft and said braking disc,
a biasing member configured to bias the braking bushing, wherein the biasing member is in a compressed state when said braking disc is in said retracted position, and wherein the biasing member is in a decompressed state when said braking disc is in said extended position,
a second braking actuator, wherein the second braking actuator is configured to provide relative rotation between said braking bushing and said braking lid, to align the braking bushing with the braking lid, such that decompression of said biasing member pushes said braking disc into the extended position.

5. The endoscope system of claim 4, wherein said braking bushing comprises indentations configured to receive protrusions of said braking lid, wherein the braking bushing is rotatable relative to the braking lid between a first configuration, wherein the indentations and the protrusions are out of alignment, thereby causing said braking bushing to compress said biasing member, and a second configuration, wherein the indentations are aligned with the protrusions, and receive the protrusions, thereby allowing the biasing member to decompress.

6. The endoscope system of claim 5, wherein decompression of said biasing member, when said protrusions align with said indentations, causes said braking disc to snap into engagement with said braking lid.

7. The endoscope system of claim 5, wherein said protrusions are at a radially outer edge of said braking lid.

8. The endoscope system of claim 7, wherein said indentations are at a radially outer edge of said braking bushing.

9. An endoscope system, comprising:
an articulation actuator;
a shaft coupled to the articulation actuator;
a braking system, comprising:
- a braking lid, wherein said shaft is received in said braking lid,
- a braking disc configured to move between an extended position, wherein the braking disc is engaged with the braking lid, and a retracted position, wherein the braking disc is disengaged from the braking lid,
- a braking bushing, wherein said braking bushing receives said shaft and said braking disc,
- a biasing member configured to bias the braking bushing, wherein the biasing member is in a compressed state when said braking disc is in said retracted position, and wherein the biasing member is in a decompressed state when said braking disc is in said extended position,
- a braking actuator, wherein the braking actuator is configured to provide relative rotation between said braking bushing and said braking lid to align the braking bushing with the braking lid, such that decompression of said biasing member pushes said braking disc into the extended position;
wherein said braking bushing is received within said biasing member.

10. The endoscope system of claim 9, wherein said braking bushing comprises indentations configured to receive protrusions of said braking lid, wherein the braking bushing is rotatable relative to the braking lid between a first configuration, wherein the indentations and the protrusions are out of alignment, thereby causing said braking bushing to compress said biasing member, and a second configuration, wherein the indentations are aligned with the protrusions, and receive the protrusions, thereby allowing the biasing member to decompress.

11. The endoscope system of claim 9, wherein said braking actuator is configured to rotate said braking lid.

12. The endoscope system of claim 9, wherein said shaft is coupled to said braking disc.

13. The endoscope system of claim 9, wherein there is a space between opposing surfaces of said braking lid and said braking disc when said braking disc is in said retracted position.

14. The endoscope system of claim 10, wherein said protrusions are at an outer periphery of said braking lid, and wherein said indentations are at an outer periphery of said braking bushing.

15. An endoscope system, comprising:
an insertion tube;
a steering knob for articulating a section of said insertion tube;
a steering shaft coupled to said steering knob, wherein said steering knob and said steering shaft are fixedly coupled, such that rotation of said steering knob causes rotation of said steering shaft;
a braking system received in said steering knob, wherein said braking system is movable relative to said steering knob and said steering shaft, said braking system comprising:
- a lid, wherein said shaft is received in said lid,
- a disc configured to move between an extended position, wherein said disc is engaged with said lid, and a retracted position, wherein said disc is disengaged from said lid,
- a bushing, wherein said bushing receives said shaft and said disc,
- a biasing member configured to bias said bushing, wherein said biasing member is in a compressed state when said disc is in said retracted position, and wherein said biasing member is in a decompressed state when said disc is in said extended position,
- an actuator, wherein said actuator is configured to provide relative rotation between said bushing and said lid to align said bushing with said lid, such that decompression of said biasing member pushes said disc into said extended position;
wherein said actuator is configured to rotate said lid.

16. The endoscope system of claim 15, wherein said shaft is coupled to said disc.

17. The endoscope system of claim 15, wherein there is a space between opposing surfaces of said lid and said disc when said disc is in said retracted position.

18. The endoscope system of claim 15, wherein said bushing and said lid are aligned when protrusions of said lid are received within indentations of said bushing.

* * * * *